United States Patent
Daphna

(10) Patent No.: US 8,500,803 B2
(45) Date of Patent: *Aug. 6, 2013

(54) HYDROPHOBIC PSEUDO-ENDOTHELIAL IMPLANTS FOR TREATING CORNEAL EDEMA

(75) Inventor: Ofer Daphna, Ashkelon (IL)

(73) Assignee: Mor Research Applications Ltd., Tel Aviv (IL)

(*) Notice: Subject to any disclaimer, the term of this patent is extended or adjusted under 35 U.S.C. 154(b) by 0 days.

This patent is subject to a terminal disclaimer.

(21) Appl. No.: 13/367,384

(22) Filed: Feb. 7, 2012

(65) Prior Publication Data

US 2012/0136437 A1 May 31, 2012

Related U.S. Application Data

(63) Continuation-in-part of application No. 12/355,781, filed on Jan. 18, 2009, now Pat. No. 8,109,997.

(51) Int. Cl.
*A61F 2/14* (2006.01)
(52) U.S. Cl.
USPC .................. 623/5.11; 623/5.16; 623/906

(58) Field of Classification Search
USPC .................................................. 623/5.11
See application file for complete search history.

(56) References Cited

U.S. PATENT DOCUMENTS

| 4,842,599 | A | * | 6/1989 | Bronstein | 623/5.15 |
|---|---|---|---|---|---|
| 4,983,181 | A | * | 1/1991 | Civerchia | 623/5.11 |
| 6,106,554 | A | * | 8/2000 | Bretton | 623/6.62 |
| 2006/0173539 | A1 | * | 8/2006 | Shiuey | 623/5.11 |
| 2008/0243156 | A1 | * | 10/2008 | John | 606/166 |

FOREIGN PATENT DOCUMENTS

| EP | 1364663 | * | 11/2003 |
|---|---|---|---|
| WO | WO 2008011566 | * | 1/2008 |
| WO | WO 2008013557 | * | 1/2008 |
| WO | WO 2009146151 | * | 12/2009 |

* cited by examiner

*Primary Examiner* — David H Willse
*Assistant Examiner* — Tiffany Shipmon
(74) *Attorney, Agent, or Firm* — Dekel Patent Ltd.; David Klein

(57) ABSTRACT

An ocular implant including a hydrophobic pseudo-endothelial implant and a binding agent applied thereto, the binding agent capable of bonding the implant to a posterior portion of a cornea such that the implant serves as a water barrier enabling dehydration of the cornea.

5 Claims, 1 Drawing Sheet

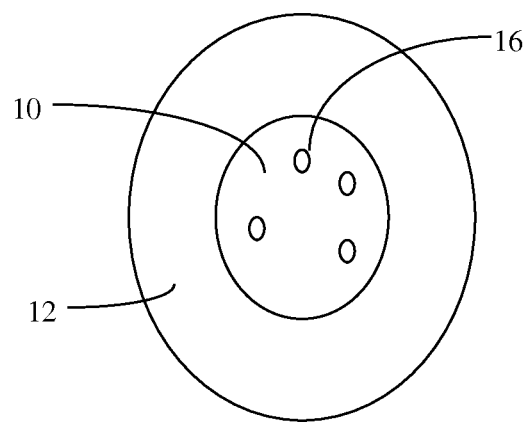

FIG. 1

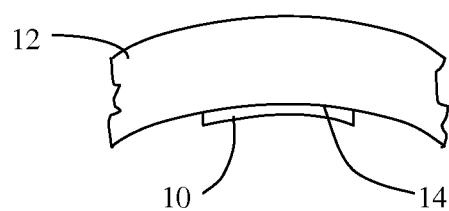

FIG. 2

```
┌─────────────────────────────────────────────┐
│ REMOVE PORTION OF POSTERIOR PORTION OF      │
│ CORNEA PRIOR TO BONDING IMPLANT TO CORNEA   │
└─────────────────────────────────────────────┘
                     │
                     ▼
┌─────────────────────────────────────────────┐
│ BOND IMPLANT TO POSTERIOR PORTION OF        │
│ CORNEA WITH BINDING AGENT                   │
│ (BINDING AGENT CAN BE PLACED ONLY AT THE    │
│ PERIPHERY OF THE IMPLANT CORNEA INTERFACE   │
│ OR ON THE ENTIRE INTERFACE SURFACE OR ANY   │
│ OTHER COMBINATION)                          │
└─────────────────────────────────────────────┘
```

FIG. 3

HYDROPHOBIC PSEUDO-ENDOTHELIAL IMPLANTS FOR TREATING CORNEAL EDEMA

CROSS-REFERENCE TO RELATED APPLICATIONS

This application is a continuation-in-part of U.S. patent application Ser. No. 12/355781, filed Jan. 18, 2009, now U.S. Pat. No. 8,109,997, which is incorporated herein by reference.

FIELD OF THE INVENTION

The present invention relates generally to endothelial implants for treating an over-hydrated, edematous cornea.

BACKGROUND OF THE INVENTION

The quality of the eye's sensory function greatly depends on the qualities of light conduction through the cornea and through the lens, and also the optical qualities of these organs and the transparency of the cornea and the eye lens, as well as other factors.

Experts in the field of ophthalmology know that corneal transparency generally depends on the ability of the cornea to remain in a dehydrated state. The cornea dehydrated state is affected by several interdependent factors, the most important of which is an active pump present in the deepest cell layer of the cornea, the endothelium. Any disruption of the endothelial function beyond a certain level as a result of surgery, trauma, infection, or congenital predisposition results in influx of water to all layers of the cornea thus distorting its transparency. The morbidity of this situation is not only a significant decrease in vision, but also at an advanced state may result in significant pain and scars, a situation known as bullous keratopathy.

Another important physiological mechanism for dehydrating the cornea is the evaporation of water from the tear film while the eye is open during wakefulness. Dehydration works by water evaporating from the tear film, which leaves behind a more concentrated solution at the surface of the eye, causing the tear film to be more hypertonic. The hypertonic tear film draws more water by osmosis from the cornea itself; the opposite is true during the night. There are some hypertonic solution eye drops available in the market to augment this mechanism but unfortunately their action is short lived due to the blinking of the eyelids.

Currently, there is no conservative treatment for an unhealthy edematous state. Several surgical procedures have evolved to address this problem: from the classical full thickness corneal transplantation to more recently developed surgical procedure called deep lamellar striping keratoplasty (DLEK) and Descemets striping endothelial keratoplasty (DSEK). In the later, a thin posterior or lenticule of stromal tissue (along with Descemet's membrane and endothelial cells attached) is removed from the cornea of a diseased eye. A similar procedure is performed on a donor eye to obtain donor tissue. When the donor tissue is placed in the recipient's eye, no sutures are required to hold the graft to the host cornea. All of these procedures have the disadvantage of being donor dependent.

SUMMARY OF THE INVENTION

The present invention relates to implantation of an artificial hydrophobic pseudo-endothelial implant to the posterior surface of the cornea for the treatment of edematous eyes, as is described more in detail hereinbelow.

There is provided in accordance with an embodiment of the present invention an ocular implant including a hydrophobic pseudo-endothelial implant and a binding agent applied thereto, the binding agent capable of bonding the implant to a posterior portion of a cornea such that the implant serves as a water barrier enabling dehydration of the cornea.

There is provided in accordance with an embodiment of the present invention a method for treating corneal edema including bonding a hydrophobic pseudo-endothelial implant to a posterior portion of a cornea with a binding agent, such that the implant serves as a water barrier enabling dehydration of the cornea.

The implant is constructed of a clear, transparent, biologically compatible material, and may be rigid, semi-rigid or foldable.

The binding agent can be placed between the implant and the posterior surface of the cornea only at the periphery of the implant cornea interface or on the entire interface surface or any other combination.

A portion of the posterior portion of the cornea may be removed (although does not have to be removed) prior to bonding the implant to the posterior portion of the cornea, such as for example, a thin posterior portion of stromal tissue along with Descemet's membrane and endothelial cells attached thereto, or just a thin posterior portion of Descemet's membrane and endothelial cells attached thereto.

The refractive state of the patient may be taken into account in the design of the implant thus enabling refractive correction along with alleviating the edematous state.

The implant can be designed in several sizes, such as from a radius of 1-2 mm up to 6 mm or more covering the whole surface of the posterior cornea or any size in between.

The thickness of the implant may be from a few microns up to more than 100 microns. The thickness may be equal through the entire implant diameter or may be different at different portions thereof in order to have refractive power, for example, being thinner at the periphery compared to the center or the opposite.

The curvature of the posterior surface of the cornea may be taken into account especially in the case of a rigid implant to provide better adhesion.

BRIEF DESCRIPTION OF THE DRAWINGS

The present invention will be understood and appreciated more fully from the following detailed description taken in conjunction with the drawings in which:

FIGS. 1 and 2 are front view and side view simplified illustrations of a hydrophobic pseudo-endothelial implant, constructed and operative in accordance with an embodiment of the present invention; and FIG. 3 is a simplified flow chart of a method for bonding the implant of FIGS. 1 and 2 to the posterior portion of the cornea, in accordance with an embodiment of the present invention.

DETAILED DESCRIPTION OF EMBODIMENTS

It is noted that Dohlman C. H., Brown S. I., Martola E. L., "Replacement Of The Endothelium With Alloplastic Material: A New Technique In Corneal Surgery", *Trans Am Acad Ophthalmol Otolaryngol.*, 1967 71(5), 851-864, herein referred to as Dohlman-Brown-Martola, describes fluid-barrier procedures performed on the eyes of patients suffering from bullous keratopathy (corneal edema). In Dohlman-Brown-Martola, a transparent silicone membrane was sutured to the posterior surface of the patient's cornea or to a corneal graft. In some of the patients, Descemet's membrane and the endothelium were removed before attaching the silicone membrane. Dohlman C. H., Freeman H. M., "Recent Advances In The Use Of Alloplastic Materials In Ocular Surgery", *Journal Documenta Ophthalmologica,* 1968, 25(1), 1-20, also discusses the use of alloplastic materials, particularly PMMA (polymethylmethacrylate) and silicone, in the eye as corneal implants. This article mentions an artificial endothelium made of transparent silicone rubber that is sutured directly to the posterior surface of the cornea, which is the same as Dohlman-Brown-Martola.

Without being tied to any theory, it is believed that the use of sutures is detrimental to the success of the hydrophobic implant. Thus, in contrast to the prior art, the present invention does not use sutures; rather different adhesive materials are used to bond the implant to the posterior portion of the cornea, as is now explained.

Reference is now made to FIGS. 1 and 2, which illustrate a hydrophobic pseudo-endothelial implant 10, constructed and operative in accordance with an embodiment of the present invention. The hydrophobic pseudo-endothelial implant 10 can be used instead of an implant from a donor in a DSEK surgery. Implant 10 serves as a water barrier enabling the dehydration of the cornea.

Implant 10 may be constructed of a clear, transparent, biologically compatible material, such as but not limited to, polymethylmethacrylate (PMMA), silicone, silicone rubber, collagen, hyaluronic acid (including the sodium, potassium and other salts thereof), hydrogel, such as acrylic or methacrylic hydrogels, e.g., hydroxyethyl methacrylate or methacrylic acid copolymer/partially hydrolyzed poly(2-hydroxyethyl methacrylate) (known as PolyHEMA), polysulfones, thermolabile materials and other relatively hard or relatively soft and flexible biologically inert optical materials, or any combination of such materials, such as a gel encapsulated in a polymer. Implant 10 may thus be rigid, semi-rigid or foldable, for example.

Prior to bonding implant 10 to the posterior portion of the cornea, as in PLK or DSEK, a thin posterior or lenticule of stromal tissue (along with Descemet's membrane and endothelial cells attached) is removed from the cornea of the patient's eye. Alternatively, as in Descemets strip endokeratoplasty, only the Descemet's membrane and endothelial cells are removed. Alternatively, the implant may be attached to the endothelium of the cornea without any posterior surface stripping.

Implant 10 is bonded to the posterior portion of the cornea 12 with a binding agent 14 (FIG. 1 shows the posterior side of the cornea 12). Binding agent 14 can be placed between the implant 10 and the posterior surface of the cornea 12 only at the periphery of the implant cornea interface or on the entire interface surface or any other combination (FIG. 3). Suitable binding agents for use in accordance with the present invention include for example, but are not limited to, poly-L-lysine and poly-D-lysine. For purposes of simplicity, each poly-L-lysine and poly-D-lysine is hereinafter referred to indiscriminately as "polylysine". Other suitable binding agents include, but are not limited to, fibronectin, laminin, type I, II, III and IV collagen, thrombospondin, polystyrene, vitronectin, polyarginine and platelet factor IV. The binding agent may include one of the above or any combination thereof. In accordance with an embodiment of the present invention, one or more of the binding agents may be conjugated with one or more cytotoxic agents which can be applied on the inner surface of the implant or its outer surface at the center or both or not at all, in order to prevent opacities that might occur by new tissue growth over the implant. Suitable cytotoxic agents include, but are not limited to, ribosomal inhibitory proteins, such as but not limited to, saporin and ricin. Other cytotoxic agents believed to be efficacious when used in connection with the present invention include, but are not limited to, antimitotic drugs such as methotrexate, 5-fluorouracil, daunomycin, doxorubicin, mitoxanthrone, vinca alkaloids, vinblastine, colchicine, and cytochasins, and ionophores such as monensin and ouabain.

In order to prevent atrophy of the cornea by total blocking of trophic material such as glucose, etc., implant 10 may be formed with one or more through holes 16 to control a small flow of fluid to and from the cornea, which will be sufficient for nutritional support but will not cause corneal edema.

In another embodiment of the present invention the outer surface of the implant 10 (facing the cornea) may have hydrophilic properties in order to further enhance adhesion to the cornea, thus creating a hydrophobic-hydrophilic implant. The refractive state of the patient may be taken into account in the design of the implant thus enabling refractive correction along with alleviating the edematous state.

In another embodiment, the hydrophobic pseudo-endothelial implant does not cover the entire posterior portion of the cornea, but rather a portion thereof. In another embodiment, the implant has optical power (negative or positive) and can be multifocal or toric, for example.

In another embodiment, the implant is introduced into the eye by injecting (or otherwise introducing) a liquid or gel-like material to the posterior portion of the cornea, such as but not limited to, a hydrogel which is a thixotropic gel.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A method for treating corneal edema of an eye that has aqueous humor posterior to a cornea, the method comprising:

bonding a hydrophobic pseudo-endothelial implant to a posterior portion of the cornea adjacent the aqueous humor with a binding agent, such that a posterior facing surface of said implant is exposed and an anterior facing surface of said implant is bonded to the cornea with said binding agent, and the implant serves as a water barrier enabling dehydration of the cornea, wherein said hydrophobic pseudo-endothelial implant does not cover entirely the posterior portion of the cornea, but rather a portion thereof.

2. The method according to claim 1, wherein said implant is introduced into the eye by introducing a liquid or gel-like material to the posterior portion of the cornea.

3. The method according to claim 1, wherein said implant has optical power.

4. An ocular implant for an eye that has aqueous humor posterior to a cornea, the implant comprising:

a hydrophobic pseudo-endothelial implant having a posterior facing surface and an anterior facing surface, and a binding agent applied to said anterior facing surface, said posterior facing surface being an exposed, aqueous-humor-interfacing surface and said anterior facing surface being a cornea-interfacing surface, wherein when said implant is installed in the eye, said binding agent bonds said implant to a posterior portion of a cornea adjacent the aqueous humor such that said implant serves as a water barrier enabling dehydration of the cornea, wherein said hydrophobic pseudo-endothelial implant does not cover entirely the posterior portion of the cornea, but rather a portion thereof.

5. An ocular implant for an eye that has aqueous humor posterior to a cornea, the implant comprising:
a hydrophobic pseudo-endothelial implant having a posterior facing surface and an anterior facing surface, and a binding agent applied to said anterior facing surface, said posterior facing surface being an exposed, aqueous-humor-interfacing surface and said anterior facing surface being a cornea-interfacing surface, wherein when said implant is installed in the eye, said binding agent bonds said implant to a posterior portion of a cornea adjacent the aqueous humor such that said implant serves as a water barrier enabling dehydration of the cornea, wherein said hydrophobic pseudo-endothelial implant has optical power.

* * * * *